(12) United States Patent
Huffstetler et al.

(10) Patent No.: US 9,931,068 B2
(45) Date of Patent: Apr. 3, 2018

(54) DRUG ELUTION FOR IN VIVO PROTECTION OF BIO-SENSING ANALYTES

(71) Applicant: Senseonics, Incorporated, Germantown, MD (US)

(72) Inventors: Philip Huffstetler, Germantown, MD (US); Jeremy Emken, Germantown, MD (US); Todd Whitehurst, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 296 days.

(21) Appl. No.: 14/464,791

(22) Filed: Aug. 21, 2014

(65) Prior Publication Data

US 2015/0057509 A1    Feb. 26, 2015

Related U.S. Application Data

(60) Provisional application No. 61/868,179, filed on Aug. 21, 2013.

(51) Int. Cl.
*A61B 5/1459* (2006.01)
*A61B 5/1473* (2006.01)
(Continued)

(52) U.S. Cl.
CPC ........ *A61B 5/1459* (2013.01); *A61B 5/14503* (2013.01); *A61B 5/1451* (2013.01);
(Continued)

(58) Field of Classification Search
CPC ... A61B 5/0031; A61B 5/1459; A61B 5/1473; A61B 5/14532; A61B 5/14865;
(Continued)

(56) References Cited

U.S. PATENT DOCUMENTS 3,854,480 A    12/1974 Zaffaroni
5,512,246 A    4/1996 Russell et al.
(Continued)

FOREIGN PATENT DOCUMENTS

CA    2 861 123 A1    8/2013
EP    1477187 B1    11/2004
(Continued)

OTHER PUBLICATIONS

Toshiaki Furuta et al., "Brominated 7-hydroxycoumarin-4-ylmethyls: Photolabile protecting groups with biologically useful cross-sections for two photon photolysis," Proc. Natl. Acad. Sci. USA, vol. 96, pp. 1193-1200, (Feb. 1999).
(Continued)

*Primary Examiner* — Eric Winakur
*Assistant Examiner* — Chu Chuan (JJ) Liu
(74) *Attorney, Agent, or Firm* — Rothwell, Figg, Ernst & Manbeck, P.C.

(57) ABSTRACT

A sensor (e.g., an optical sensor) that may be implanted within a living animal (e.g., a human) and may be used to measure an analyte (e.g., glucose or oxygen) in a medium (e.g., interstitial fluid, blood, or intraperitoneal fluid) within the animal. The sensor may include a sensor housing, an analyte indicator covering at least a portion of the sensor housing, and one or more therapeutic agents. The one or more therapeutic agents may reduce deterioration of the analyte indicator. The one or more therapeutic agents may be incorporated within the analyte indicator, a membrane covering at least a portion of the analyte indicator, and/or one or more drug eluting polymer matrices, which may be external to or within the sensor housing.

40 Claims, 14 Drawing Sheets

(51) Int. Cl.
  *A61B 5/145* (2006.01)
  *A61B 5/1455* (2006.01)
  *A61B 5/00* (2006.01)
  *A61M 37/00* (2006.01)

(52) U.S. Cl.
  CPC ......... *A61B 5/1473* (2013.01); *A61B 5/14532* (2013.01); *A61B 5/14542* (2013.01); *A61B 5/14546* (2013.01); *A61B 5/14556* (2013.01); *A61B 5/4839* (2013.01); *A61B 5/6847* (2013.01); *A61M 37/00* (2013.01); *A61M 2205/3303* (2013.01); *A61M 2205/3306* (2013.01); *A61M 2230/005* (2013.01)

(58) Field of Classification Search
  CPC ... A61B 5/0059; A61B 5/1455; A61B 5/1451; A61B 5/14503; A61B 5/14542; A61B 5/14546; A61B 5/14556; A61B 5/4839; A61B 5/6847
  USPC .................................. 600/309, 345, 347, 365
  See application file for complete search history.

(56) References Cited

U.S. PATENT DOCUMENTS

| | | | |
|---|---|---|---|
| 5,517,313 A | 5/1996 | Colvin, Jr. | |
| 6,051,576 A | 4/2000 | Ashton et al. | |
| 6,330,464 B1* | 12/2001 | Colvin, Jr. | A61B 5/14532 600/316 |
| 2003/0199837 A1 | 10/2003 | Vachon | |
| 2006/0008500 A1 | 1/2006 | Chavan et al. | |
| 2010/0249783 A1 | 9/2010 | Trieu | |
| 2011/0077490 A1 | 3/2011 | Simpson et al. | |
| 2011/0236989 A1* | 9/2011 | Suri | G01N 21/6428 436/172 |
| 2012/0187594 A1 | 7/2012 | Utkhede et al. | |

FOREIGN PATENT DOCUMENTS

| | | |
|---|---|---|
| EP | 1637164 A2 | 3/2006 |
| EP | 2303227 A2 | 4/2011 |
| EP | 2416783 A1 | 2/2012 |
| WO | 97/19344 A1 | 5/1997 |
| WO | 2009/139924 A2 | 11/2009 |
| WO | 2010/115615 A1 | 10/2010 |
| WO | 2010/123972 A1 | 10/2010 |
| WO | 2012/125814 A2 | 9/2012 |
| WO | 2013/114011 A1 | 8/2013 |
| WO | 2013/119951 A2 | 8/2013 |

OTHER PUBLICATIONS

Jeremiah A. Johnson et al., "Synthesis of Photocleavable Liner Macromonomers by ATRP and Star Macromonomers by a Tandem ATRP—Click Reaction: Precursors to Photodegradable Model Networks," Macromolecules, vol. 40, pp. 3589-3598, (2007).

Nobuhiko Yui et al., "Photo-responsive degradation of heterogeneous hydrogels comprising crosslinked hyaluronic acid and lipid microspheres for temporal drug delivery," Journal of Controlled Release, vol. 26, pp. 141-145, (1993).

* cited by examiner

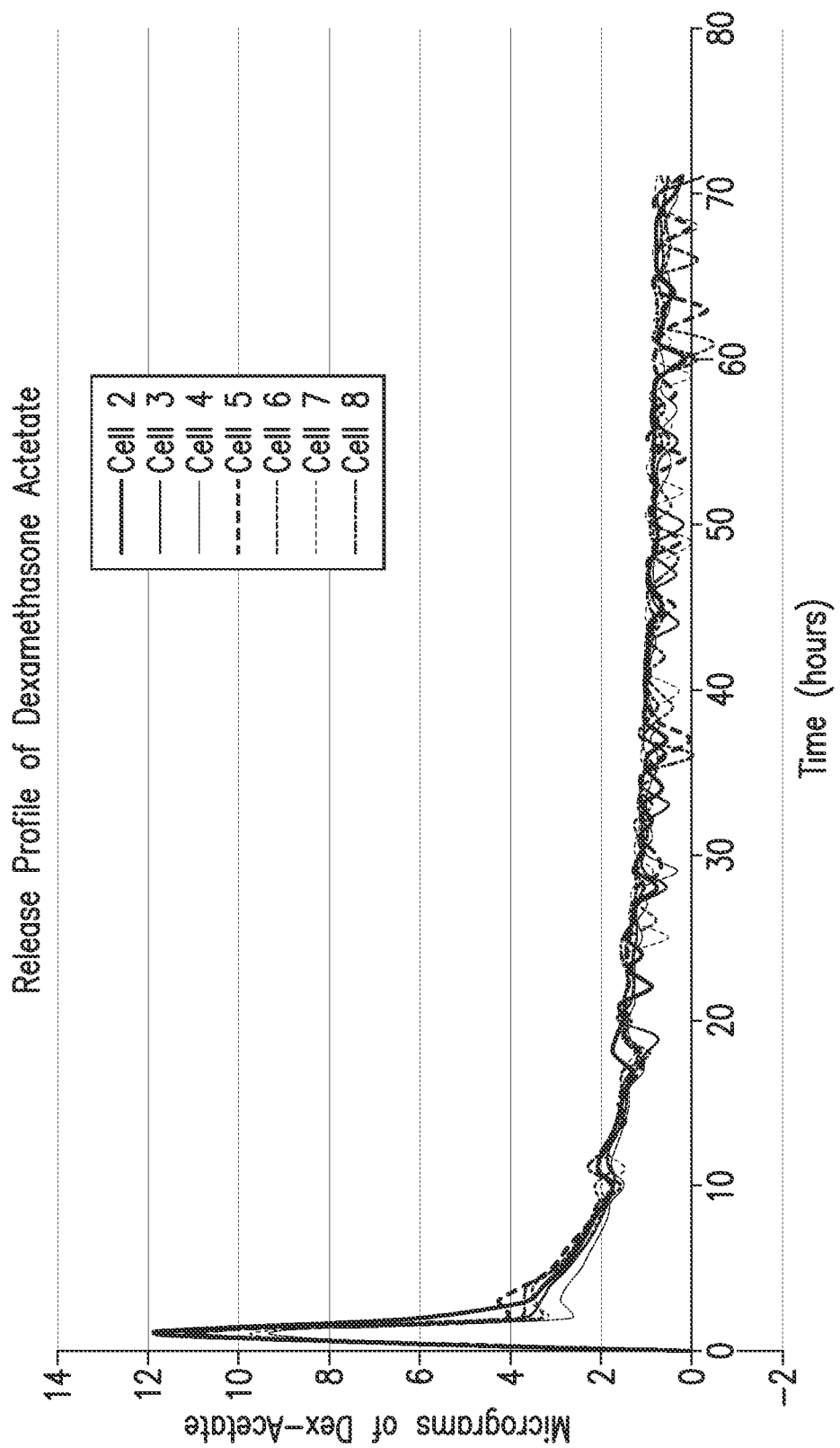

DRUG ELUTION FOR IN VIVO PROTECTION OF BIO-SENSING ANALYTES

CROSS-REFERENCE TO RELATED APPLICATIONS

The present application claims the benefit of priority to U.S. Provisional Application Ser. No. 61/868,179, filed on Aug. 21, 2013, which is incorporated herein by reference in its entirety.

BACKGROUND

Field of Invention

The present invention relates generally to measuring an analyte in a medium of a living animal using a system including a sensor implanted or inserted into the living animal. Specifically, the present invention relates to a sensor that utilizes one or more therapeutic agents, which may be incorporated within a drug eluting polymer matrix, an analyte indicator, and/or a membrane covering at least a portion of the analyte indicator.

Discussion of the Background

A sensor may be implanted within a living animal (e.g., a human) and used to measure an analyte (e.g., glucose, oxygen, cardiac markers, low-density lipoprotein (LDL), high-density lipoprotein (HDL), or triglycerides) in a medium (e.g., interstitial fluid (ISF), blood, or intraperitoneal fluid) within the living animal. The sensor may include a light source (e.g., a light-emitting diode (LED) or other light emitting element), indicator molecules, and a photodetector (e.g., a photodiode, phototransistor, photoresistor or other photosensitive element). Examples of implantable sensors employing indicator molecules to measure an analyte are described in U.S. Pat. Nos. 5,517,313 and 5,512,246, which are incorporated herein by reference in their entirety.

A sensor may include an analyte indicator, which may be in the form of indicator molecules embedded in a graft (i.e., layer or matrix). For example, in an implantable fluorescence-based glucose sensor, fluorescent indicator molecules may reversibly bind glucose and, when irradiated with excitation light (e.g., light having a wavelength of approximately 378 nm), emit an amount of light (e.g., light in the range of 400 to 500 nm) that depends on whether glucose is bound to the indicator molecule.

If a sensor is implanted in the body of a living animal, the animal's immune system may begin to attack the sensor. For instance, if a sensor is implanted in a human, white blood cells may attack the sensor as a foreign body, and, in the initial immune system onslaught, neutrophils may be the primary white blood cells attacking the sensor. The defense mechanism of neutrophils includes the release of highly caustic substances known as reactive oxygen species. The reactive oxygen species include, for example, hydrogen peroxide.

Hydrogen peroxide and other reactive oxygen species may degrade the indicator molecules of an analyte indicator. For instance, in indicator molecules having a boronate group, hydrogen peroxide may degrade the indicator molecules by oxidizing the boronate group, thus disabling the ability of the indicator molecule to bind glucose.

Glucocorticoids are used with cardiac pace makers and eye surgery to reduce inflammation. For instance, the following European patent application publications describe pace-maker leads and controlled release of steroids: EP2416783 A1 ("Improved glucocorticoid therapy"), EP1477187 B1 ("Formulation for controlled release of drugs by combining hydrophilic and hydrophobic agents"), EP1637164 A2 ("Improved formulation for controlled release of drugs by combining hydrophilic and hydrophobic agents"), and EP2303227 A2 ("Controlled release corticosteroid compositions and methods for the treatment of optic disorders"). However, these devices do not have analyte indicators, and the glucocorticoid is not used to reduce degradation of an analyte indicator. Instead, the glucocorticoid is used to stop scar tissue from building up.

There is presently a need in the art for improvements in reducing analyte indicator degradation.

SUMMARY

The present invention overcomes the disadvantages of prior systems by providing, among other advantages, reduced analyte indicator degradation.

One aspect of the present invention provides a sensor that may be for implantation or insertion within a living animal and measurement of an analyte in a medium within the living animal. The sensor may include a sensor housing, an analyte indicator covering at least a portion of the sensor housing, and one or more therapeutic agents that reduce deterioration of the analyte indicator.

In some embodiments, the sensor may include at least one drug eluting polymer matrix, and the one or more therapeutic agents may be dispersed within the drug eluting polymer matrix. In some embodiments, the drug eluting polymer matrix may cover at least a portion of the sensor housing. In some embodiments, the drug eluting polymer matrix may be within the sensor housing. The sensor housing may be perforated to allow elution of the one or more therapeutic agents from a drug eluting polymer matrix within the sensor housing.

In some embodiments, the one or more therapeutic agents may be incorporated in the analyte indicator. In some embodiments, the sensor may include a membrane covering at least a portion of the analyte indicator, and the one or more therapeutic agents are incorporated within the membrane.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIG. 10 illustrates the release profile of dexamethasone acetate from a drug-eluting polymer matrix according to one embodiment.

DETAILED DESCRIPTION OF PREFERRED EMBODIMENTS

Figure 1:
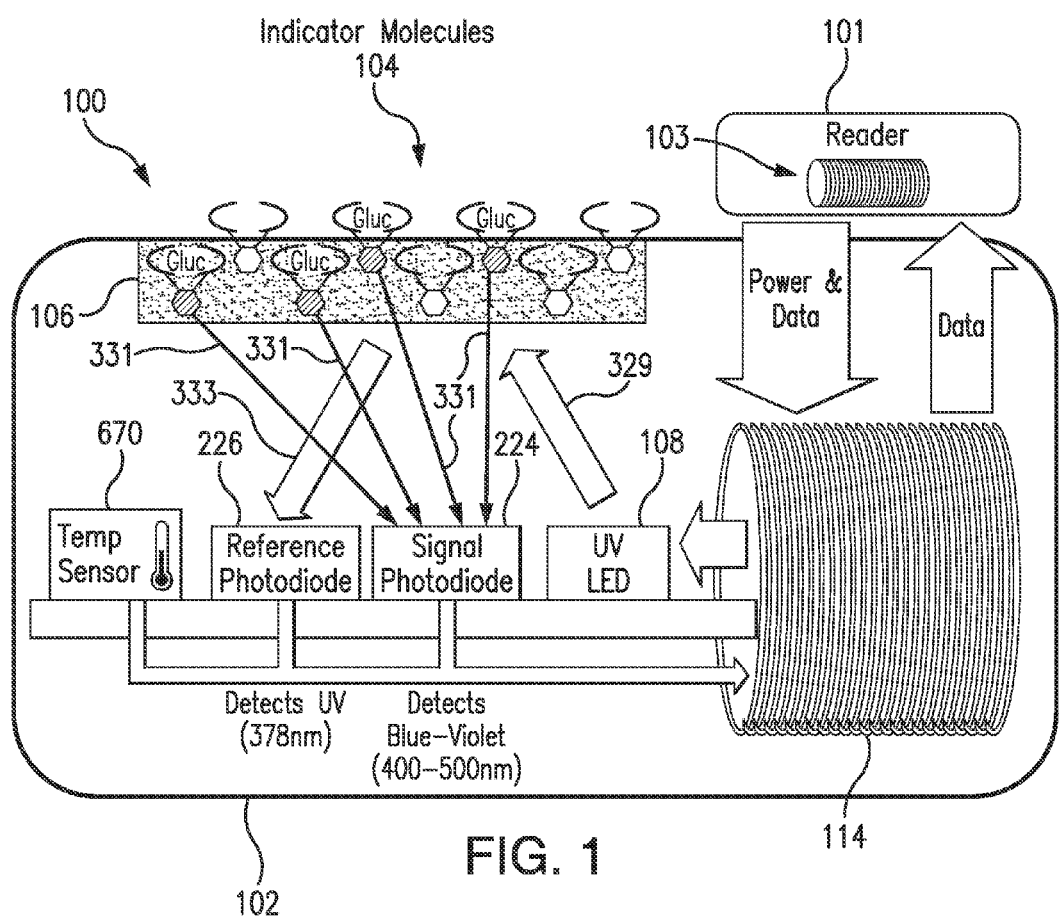
FIG. 1 is a schematic view illustrating a sensor system embodying aspects of the present invention.

FIG. 1 is a schematic view of a sensor system embodying aspects of the present invention. In one non-limiting embodiment, the system includes a sensor 100 and an external transceiver 101. In the embodiment shown in FIG. 1, the sensor 100 may be implanted in a living animal (e.g., a living human). The sensor 100 may be implanted, for example, in a living animal's arm, wrist, leg, abdomen, peritoneum, or other region of the living animal suitable for sensor implantation. For example, in one non-limiting embodiment, the sensor 100 may be implanted beneath the skin (i.e., in the subcutaneous or peritoneal tissues). In some embodiments, the sensor 100 may be an optical sensor. In some embodiments, the sensor 100 may be a chemical or biochemical sensor.

A transceiver 101 may be an electronic device that communicates with the sensor 100 to power the sensor 100 and/or receive measurement information (e.g., photodetector and/or temperature sensor readings) from the sensor 100. The measurement information may include one or more readings from one or more photodetectors of the sensor and/or one or more readings from one or more temperature sensors of the sensors. In some embodiments, the transceiver 101 may calculate analyte (e.g., glucose) concentrations from the measurement information received from the sensor 100.

In some non-limiting embodiments, the transceiver 101 may be a handheld device or an on-body/wearable device. For example, in some embodiments where the transceiver 101 is an on-body/wearable device, the transceiver 101 may be held in place by a band (e.g., an armband or wristband) and/or adhesive, and the transceiver 101 may convey (e.g., periodically, such as every two minutes, and/or upon user initiation) measurement commands (i.e., requests for measurement information) to the sensor 100. In some embodiments where the transceiver 101 is a handheld device, positioning (i.e., hovering or swiping/waving/passing) the transceiver 101 within range over the sensor implant site (i.e., within proximity of the sensor 100) may cause the transceiver 101 to automatically convey a measurement command to the sensor 100 and receive a reading from the sensor 100.

In some embodiments, the transceiver 101 may include an inductive element 103, such as, for example, a coil. The transceiver 101 may generate an electromagnetic wave or electrodynamic field (e.g., by using a coil) to induce a current in an inductive element 114 of the sensor 100, which powers the sensor 100. The transceiver 101 may also convey data (e.g., commands) to the sensor 100. For example, in a non-limiting embodiment, the transceiver 101 may convey data by modulating the electromagnetic wave used to power the sensor 100 (e.g., by modulating the current flowing through a coil 103 of the transceiver 101). The modulation in the electromagnetic wave generated by the transceiver 101 may be detected/extracted by the sensor 100. Moreover, the transceiver 101 may receive data (e.g., measurement information) from the sensor 100. For example, in a non-limiting embodiment, the transceiver 101 may receive data by detecting modulations in the electromagnetic wave generated by the sensor 100, e.g., by detecting modulations in the current flowing through the coil 103 of the transceiver 101.

The inductive element 103 of the transceiver 101 and the inductive element 114 of the sensor 100 may be in any configuration that permits adequate field strength to be achieved when the two inductive elements are brought within adequate physical proximity.

In some embodiments, the sensor 100 includes a sensor housing 102 (i.e., body, shell, capsule, or encasement), which may be rigid and biocompatible. In exemplary embodiments, sensor housing 102 may be formed from a suitable, optically transmissive polymer material, such as, for example, acrylic polymers (e.g., polymethylmethacrylate (PMMA)).

In some embodiments, sensor 100 may include an analyte indicator. In some non-limiting embodiments, the analyte indicator may be a polymer graft 106 coated, diffused, adhered, or embedded on at least a portion of the exterior surface of the sensor housing 102. The polymer graft 106 may cover the entire surface of sensor housing 102 or only one or more portions of the surface of housing 102. As an alternative to coating the graft 106 on the outer surface of sensor housing 102, the graft 106 may be disposed on the outer surface of the sensor housing 102 in other ways, such as by deposition or adhesion. In some embodiments, the polymer graft 106 may be a fluorescent glucose indicating polymer. In one non-limiting embodiment, the polymer is biocompatible and stable, grafted onto the surface of sensor housing 102, designed to allow for the direct measurement of glucose in interstitial fluid (ISF), blood, or intraperitoneal fluid after implantation of the sensor 100.

In some embodiments, the analyte indicator (e.g., polymer graft 106) of the sensor 100 may include indicator molecules 104. The indicator molecules 104 may be distributed throughout the entire graft 106 or only throughout one or more portions of the graft 106. The indicator molecules 104 may be fluorescent indicator molecules (e.g., TFM having the chemical name 9-[N-[6-(4,4,5,5,-tetramethyl-1,3,2-dioxaborolano)-3-(trifluoromethyl)benzyl]-N-[3-(methacrylamido)propylamino]methyl]-10-[N-[6-(4,4,5,5,-tetramethyl-1,3,2-dioxaborolano)-3-(trifluoromethyl)benzyl]-N-[2-(carboxyethyl)amino]methyl]anthracene sodium salt) or light absorbing, non-fluorescent indicator molecules. In some embodiments, the indicator molecules 104 may reversibly bind an analyte (e.g., glucose, oxygen, cardiac markers, low-density lipoprotein (LDL), high-density lipoprotein (HDL), or triglycerides). When an indicator molecule 104 has bound an analyte, the indicator molecule may become fluorescent, in which case the indicator molecule 104 is capable of absorbing (or being excited by) excitation light 329 and emitting light 331. In one non-limiting embodiment, the excitation light 329 may have a wavelength of approximately 378 nm, and the emission light 331 may have a wavelength in the range of 400 to 500 nm. When no analyte is bound, the indicator molecule 104 may be only weakly fluorescent.

In some embodiments, the sensor 100 may include a light source 108, which may be, for example, a light emitting diode (LED) or other light source that emits radiation, including radiation over a range of wavelengths that interact with the indicator molecules 104. In other words, the light source 108 may emit the excitation light 329 that is absorbed by the indicator molecules in the matrix layer/polymer 104. As noted above, in one non-limiting embodiment, the light source 108 may emit excitation light 329 at a wavelength of approximately 378 nm.

In some embodiments, the sensor 100 may also include one or more photodetectors (e.g., photodiodes, phototransistors, photoresistors or other photosensitive elements). For example, in the embodiment illustrated in FIG. 1, sensor 100 has a first photodetector 224 and a second photodetector 226. However, this is not required, and, in some alternative embodiments, the sensor 100 may only include the first photodetector 224. In the case of a fluorescence-based sensor, the one or more photodetectors may be sensitive to fluorescent light emitted by the indicator molecules 104 such that a signal is generated by a photodetector (e.g., photodetector 224) in response thereto that is indicative of the level of fluorescence of the indicator molecules and, thus, the amount of analyte of interest (e.g., glucose).

Some part of the excitation light 329 emitted by the light source 108 may be reflected from the polymer graft 106 back into the sensor 100 as reflection light 333, and some part of the absorbed excitation light may be emitted as emitted (fluoresced) light 331. In one non-limiting embodiment, the emitted light 331 may have a different wavelength than the wavelength of the excitation light 329. The reflected light 333 and emitted (fluoresced) light 331 may be absorbed by the one or more photodetectors (e.g., first and second photodetectors 224 and 226) within the body of the sensor 100.

Each of the one or more photodetectors may be covered by a filter 112 (see FIG. 3) that allows only a certain subset of wavelengths of light to pass through. In some embodiments, the one or more filters 112 may be thin glass filters. In some embodiments, the one or more filters 112 may be thin film (e.g., dichroic) filters deposited on the glass and may pass only a narrow band of wavelengths and otherwise reflect most of the received light. In some embodiments, the filters may be thin film (dichroic) filters deposited directly onto the photo detectors and may pass only a narrow band of wavelengths and otherwise reflect most of the light received thereby. The filters 112 may be identical (e.g., both filters 112 may allow signals to pass) or different (e.g., one filter 112 may be a reference filter and another filter 112 may be a signal filter).

In one non-limiting embodiment, the second (reference) photodetector 226 may be covered by a reference photodiode filter that passes light at the same wavelength as is emitted from the light source 108 (e.g., 378 nm). The first (signal) photodetector 224 may detect the amount of fluoresced light 331 that is emitted from the molecules 104 in the graft 106. In one non-limiting embodiment, the peak emission of the indicator molecules 104 may occur around 435 nm, and the first photodetector 224 may be covered by a signal filter that passes light in the range of about 400 nm to 500 nm. In some embodiments, higher glucose levels/concentrations correspond to a greater amount of fluorescence of the molecules 104 in the graft 106, and, therefore, a greater number of photons striking the first photodetector 224.

In some embodiments, sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components, may be fabricated in the semiconductor substrate 116 with the remainder of the circuitry is secured to the semiconductor substrate 116, which may provide communication paths between the various secured components. In some embodiments, circuitry of the sensor 100 may incorporate some or all of the structure described in U.S. patent application Ser. No. 13/650,016, which is incorporated herein by reference in its entirety, with particular reference to FIG. 11D.

In some embodiments, the one or more photodetectors (e.g., photodetectors 224 and 226) may be mounted on the semiconductor substrate 116, but, in some preferred embodiments, the one or more photodetectors may be fabricated in the semiconductor substrate 116. In some embodiments, the light source 108 may be mounted on the semiconductor substrate 116. For example, in a non-limiting embodiment, the light source 108 may be flip-chip mounted on the semiconductor substrate 116. However, in some embodiments, the light source 108 may be fabricated in the semiconductor substrate 116.

Figure 2:
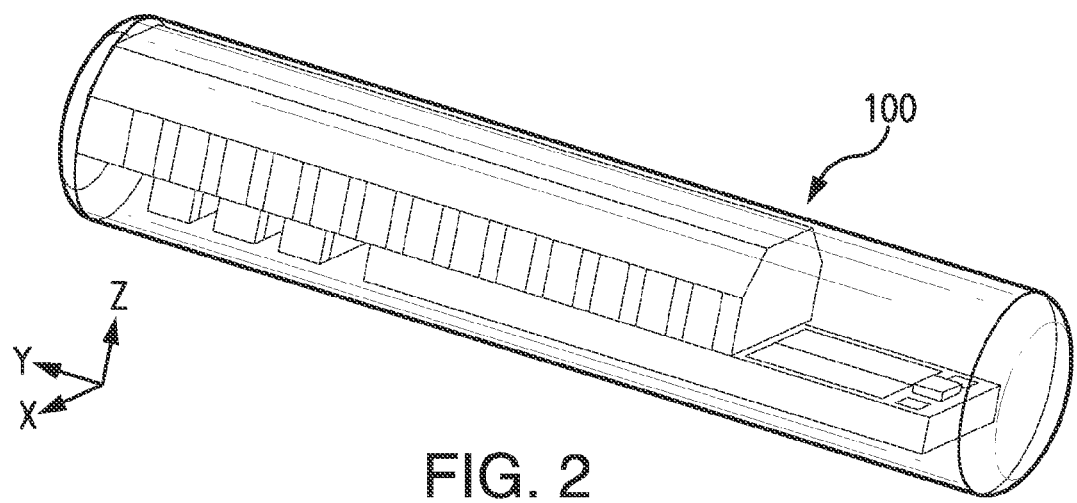
FIG. 2 illustrates a perspective view of a sensor embodying aspects of the present invention.
Figure 3:
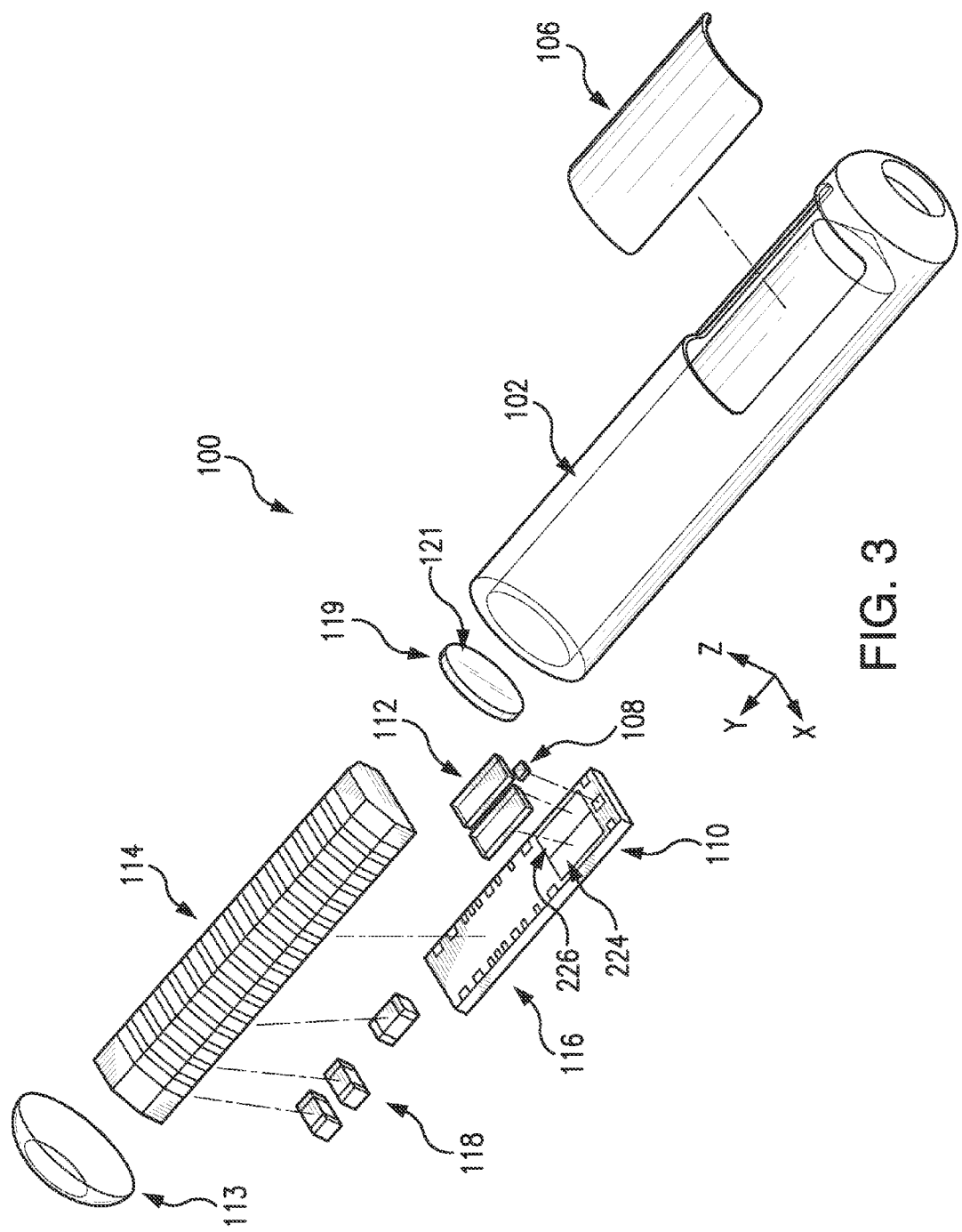
FIG. 3 illustrates an exploded view of a sensor embodying aspects of the present invention.

FIGS. 2-7 illustrate a non-limiting embodiment of a sensor 100 embodying aspects of the present invention that may be used in the sensor system illustrated in FIG. 1. FIGS. 2 and 3 illustrate perspective and exploded views, respectively, of the non-limiting embodiment of the sensor 100.

In some embodiments, as illustrated in FIG. 3, the sensor housing 102 may include an end cap 113. In some embodiments, the sensor 100 may include one or more capacitors 118. The one or more capacitors 118 may be, for example, one or more tuning capacitors and/or one or more regulation capacitors. The one or more capacitors 118 may be too large for fabrication in the semiconductor substrate 116 to be practical. Further, the one or more capacitors 118 may be in addition to one or more capacitors fabricated in the semiconductor substrate 116.

In some embodiments, as illustrated in FIG. 3, the sensor 100 may include a reflector 119 (i.e., mirror). Reflector 119 may be attached to the semiconductor substrate 116 at an end thereof. In a non-limiting embodiment, reflector 119 may be attached to the semiconductor substrate 116 so that a face portion 121 of reflector 119 is generally perpendicular to a top side of the semiconductor substrate 116 (i.e., the side of semiconductor substrate 116 on or in which the light source 108 and one or more photodetectors 110 are mounted or fabricated) and faces the light source 108. The face 121 of the reflector 119 may reflect radiation emitted by light source 108. In other words, the reflector 119 may block radiation emitted by light source 108 from exiting the axial end of the sensor 100.

According to one aspect of the invention, an application for which the sensor 100 was developed (although by no means the only application for which it is suitable) is measuring various biological analytes in the living body of an animal (including a human). For example, sensor 100 may be used to measure glucose, oxygen, toxins, pharmaceuticals or other drugs, hormones, and other metabolic analytes in, for example, the human body.

The specific composition of the polymer graft 106 and the indicator molecules 104 may vary depending on the particular analyte the sensor is to be used to detect and/or where the sensor is to be used to detect the analyte (e.g., in the in subcutaneous tissues, blood, or peritoneum). Preferably, however, graft 106 should facilitate exposure of the indicator molecules to the analyte. Also, it is preferred that the optical characteristics of the indicator molecules (e.g., the level of fluorescence of fluorescent indicator molecules) be a function of the concentration of the specific analyte to which the indicator molecules are exposed.

Figure 4:
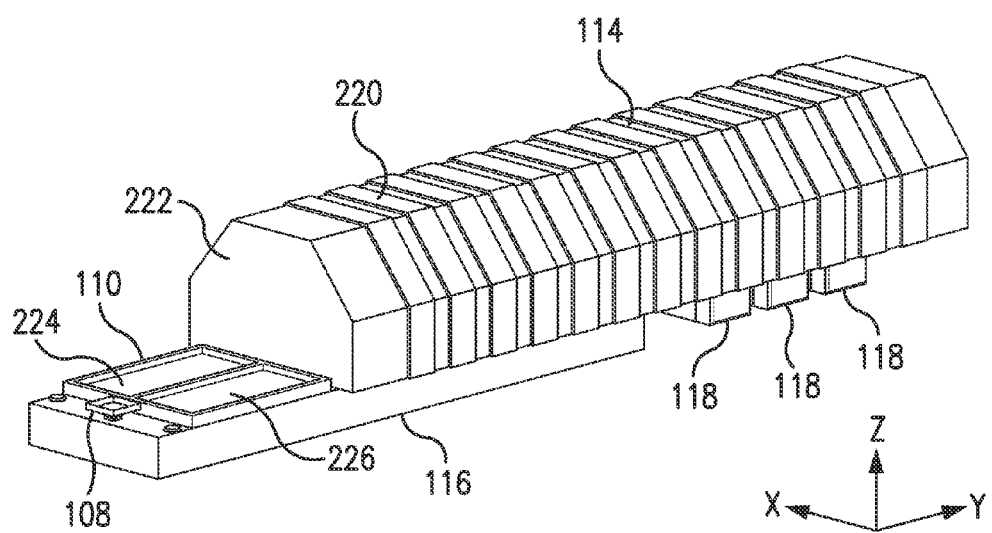
FIGS. 4 and 5 illustrate perspective views of sensor components within the sensor body/shell/capsule of a sensor embodying aspects of the present invention.
Figure 5:
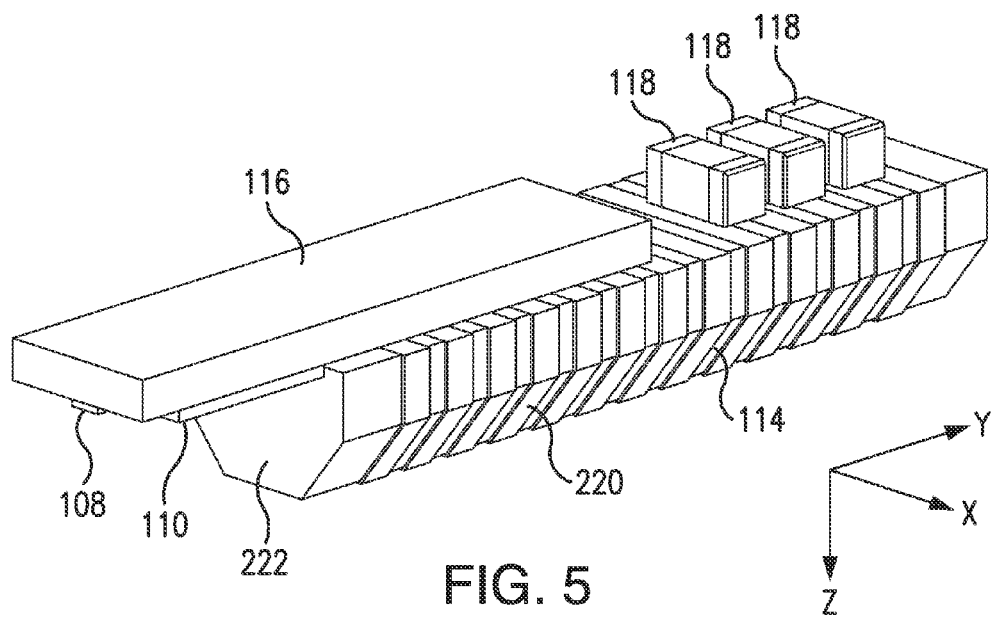

FIGS. 4 and 5 illustrate perspective views of the sensor 100. In FIGS. 4 and 5, the sensor housing 102, filters 112, and the reflector 119, which may be included in some embodiments of the sensor 100, are not illustrated. As shown in the illustrated embodiment, the inductive element 114 may comprise a coil 220. In one embodiment, coil 220 may be a copper coil, but other conductive materials, such as, for example, screen printed gold, may alternatively be used. In some embodiments, the coil 220 is formed around a ferrite core 222. Although core 222 is ferrite in some embodiments, in other embodiments, other core materials may alternatively be used. In some embodiments, coil 220 is not formed around a core. Although coil 220 is illustrated as a cylindrical coil in FIGS. 4 and 5, in other embodiments, coil 220 may be a different type of coil, such as, for example, a flat coil.

In some embodiments, coil 220 is formed on ferrite core 222 by printing the coil 220 around the ferrite core 222 such that the major axis of the coil 220 (magnetically) is parallel to the longitudinal axis of the ferrite core 222. A non-limiting example of a coil printed on a ferrite core is described in U.S. Pat. No. 7,800,078, which is incorporated herein by reference in its entirety. In an alternative embodiment, coil 220 may be a wire-wound coil. However, embodiments in which coil 220 is a printed coil as opposed to a wire-wound coil are preferred because each wire-wound coil is slightly different in characteristics due to manufacturing tolerances, and it may be necessary to individually tune each sensor that uses a wire-wound coil to properly match the frequency of operation with the associated antenna. Printed coils, by contrast, may be manufactured using automated techniques that provide a high degree of reproducibility and homogeneity in physical characteristics, as well as reliability, which is important for implant applications, and increases cost-effectiveness in manufacturing.

In some embodiments, a dielectric layer may be printed on top of the coil 220. The dielectric layer may be, in a non-limiting embodiment, a glass based insulator that is screen printed and fired onto the coil 220. In an exemplary embodiment, the one or more capacitors 118 and the semiconductor substrate 116 may be mounted on vias through the dielectric.

In the illustrated embodiment, the one or more photodetectors 110 include a first photodetector 224 and a second photodetector 226. First and second photodetectors 224 and 226 may be mounted on or fabricated in the semiconductor substrate 116.

Figure 6:
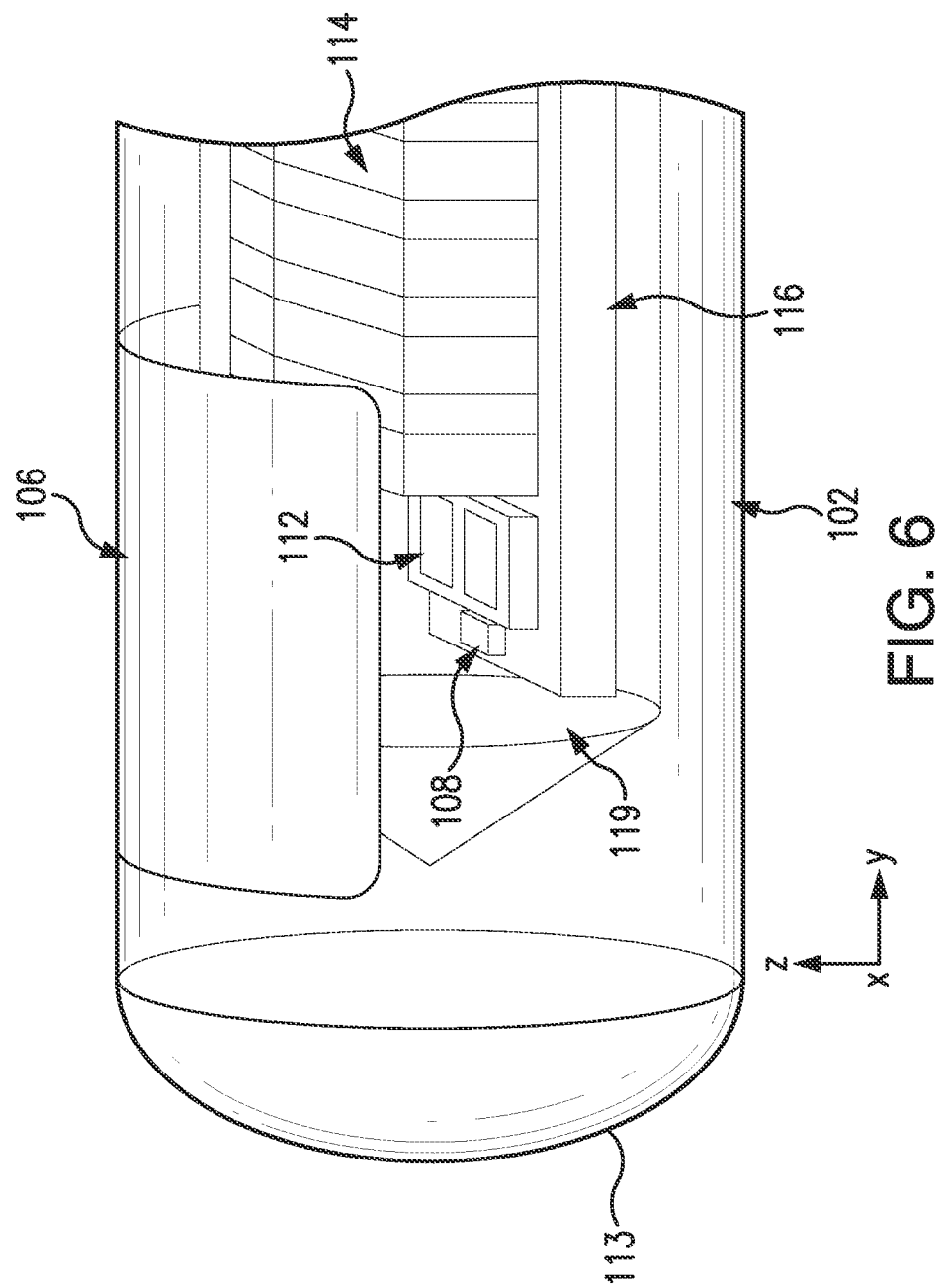
FIG. 6 illustrates a side view of a sensor embodying aspects of the present invention.
Figure 7:
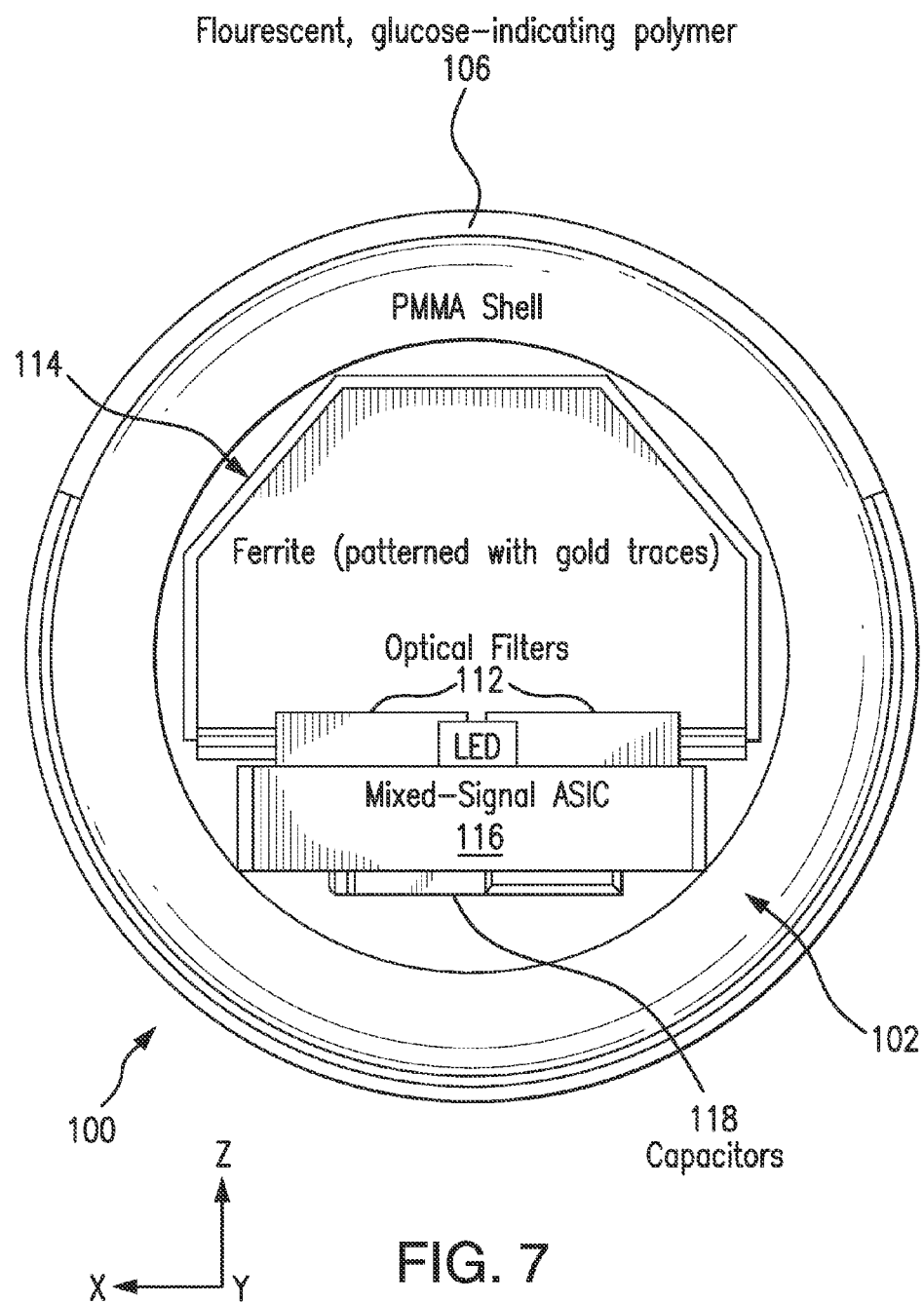
FIG. 7 illustrates a cross-sectional end view of a sensor embodying aspects of the present invention.

FIGS. 6 and 7 illustrate side and cross-sectional views, respectively, of the sensor 100 according to one embodiment. As illustrated in FIGS. 6 and 7, the light source 108 may be positioned to emit light that travels within the sensor housing 102 and reaches the indicator molecules 104 of the polymer graft 106, and the photodetectors 110, which may be located beneath filters 112, may be positioned to receive light from the indicator molecules 104 of the polymer graft 106.

The implantation or insertion of a medical device, such as a bio-sensor, into a user/patient's body can cause the body to exhibit adverse physiological reactions that are detrimental to the functioning of the device. The reactions may range from infections due to implantation surgery to the immunological response of a foreign object implanted in the body. That is, the performance of the implantable bio-sensor can be hindered or permanently damaged in vivo via the immunological response to an infection or the device itself. In particular, the performance of the analyte indicator may be deteriorated by the immunological response of the body into which the sensor 100 is implanted. For example, as explained above, white blood cells, including neutrophils, may attack an implanted sensor 100. The neutrophils release, inter alia, hydrogen peroxide, which may degrade indicator molecules 104 (e.g., by oxidizing a boronate group of an indicator molecule and disabling the ability of the indicator molecule to bind glucose).

The sensor 100 may include one or more drug-eluting polymer matrices. In one embodiment, the drug eluting polymer matrix may cover at least a portion of the sensor housing 102. One or more therapeutic agents may be dispersed within the drug eluting polymer matrix (e.g., an inert polymer matrix). In some embodiments, the one or more therapeutic agents may reduce or stop the migration of neutrophils from entering the wound space and, thus, reduce or stop the production of hydrogen peroxide and fibrotic encapsulation. Accordingly, in some embodiments, the one or more therapeutic agents may reduce deterioration of the analyte indicator (e.g., polymer graft 106).

Figure 8:
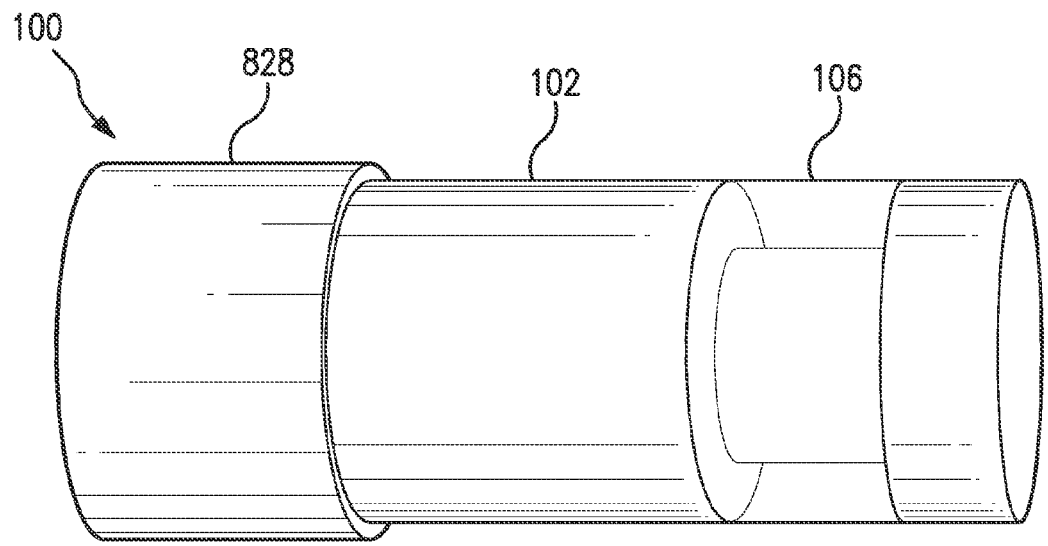
FIG. 8 illustrates a sensor having a dip coated drug-eluting polymer matrix embodying aspects of the present invention.

In some non-limiting embodiments, the drug-eluting polymer matrix may be applied to the sensor housing 102 via dip coating. FIG. 8 illustrates a sensor 100 having a dip coated drug-eluting polymer matrix 828. In the embodiment illustrated in FIG. 8, the dip coated drug-eluting polymer matrix 828 covers a portion of the sensor housing 102. However, this is not required, and, in alternative embodiments, the dip coated drug-eluting polymer matrix 828 may cover a different portion of the sensor housing 102 or the entire sensor housing 102. In some non-limiting embodiments, as an alternative to dip coating, the drug-eluting polymer matrix may be applied to the sensor housing 102 via spray coating.

Figure 9A:
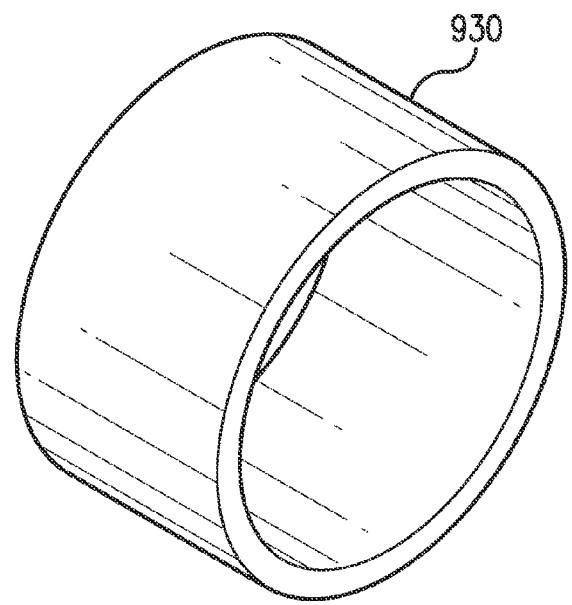
FIGS. 9A-9G illustrate examples of sensors having a preformed drug-eluting polymer matrix embodying aspects of the present invention.
Figure 9B:
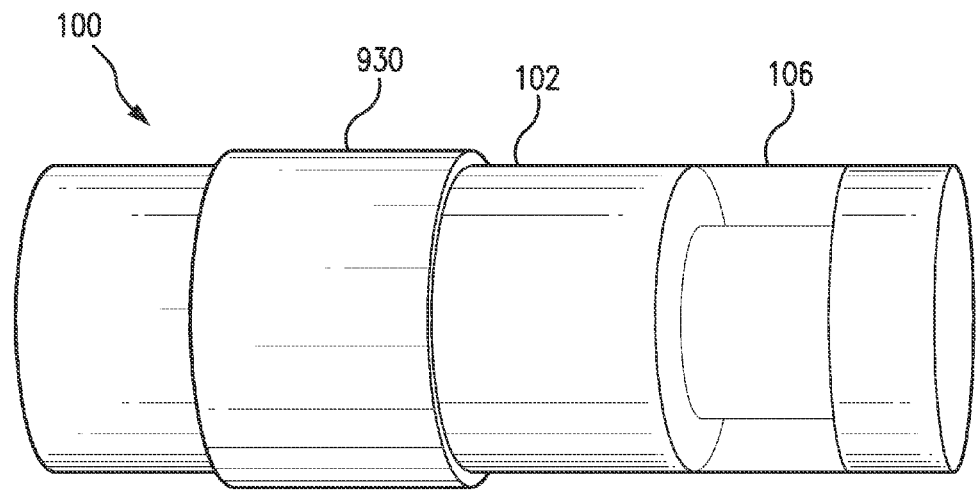
Figure 9C:
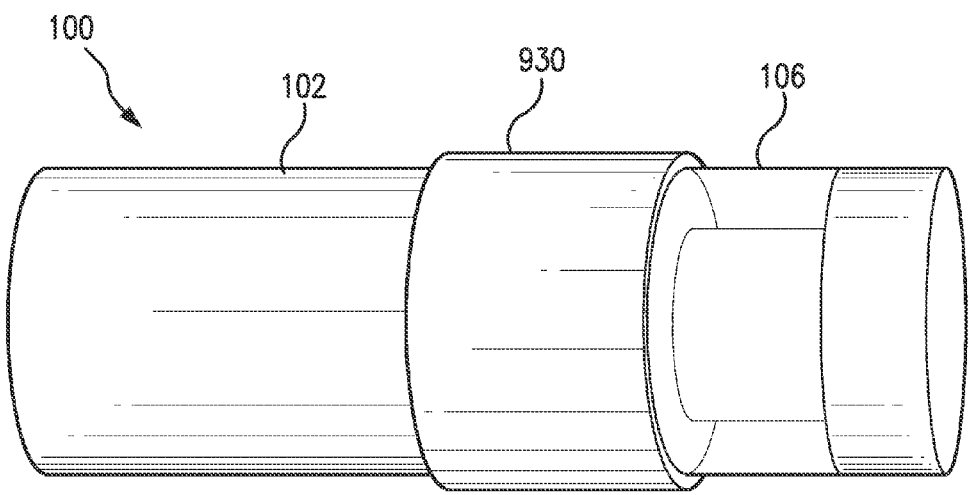

In some non-limiting embodiments, as an alternative to a dip or spray coated drug-eluting polymer matrix, the drug-eluting polymer matrix may have a pre-formed shape such as, for example, a ring or sleeve. Other pre-formed shapes are possible, such as, for example and without limitation, a shell (e.g., conformal shell), cylinder, or any suitable monolith (e.g. rectangular). FIG. 9A illustrates an example of a preformed, ring-shaped drug-eluting polymer matrix 930 that covers a portion of sensor housing 102. As illustrated in FIG. 9B, the ring-shaped drug-eluting polymer matrix 930 may wrap around a portion of the sensor housing 102. In some alternative embodiments, the ring-shaped drug-eluting polymer matrix 930 may be wider or narrower than the ring-shaped drug-eluting polymer matrix 930 illustrated in FIG. 9B. For instance, in one non-limiting embodiment, the preformed, ring-shaped drug-eluting polymer matrix 930 may have a width equal to the width of the sensor 100 (except for the portion constituting the polymer graft 106) and wrap around the entire width of the sensor 100. In another non-limiting embodiment, as illustrated in FIG. 9C, the ring-shaped drug-eluting polymer matrix 930 may be located adjacent the polymer matrix 106. Although the ring-shaped drug-eluting polymer matrix 930 is located on one side of the polymer matrix 106 in embodiment illustrated in FIG. 9C, the ring-shaped drug-eluting polymer matrix 930 could be located to the other side of the polymer matrix 106 or on both sides of the polymer matrix 930.

Figure 9D:
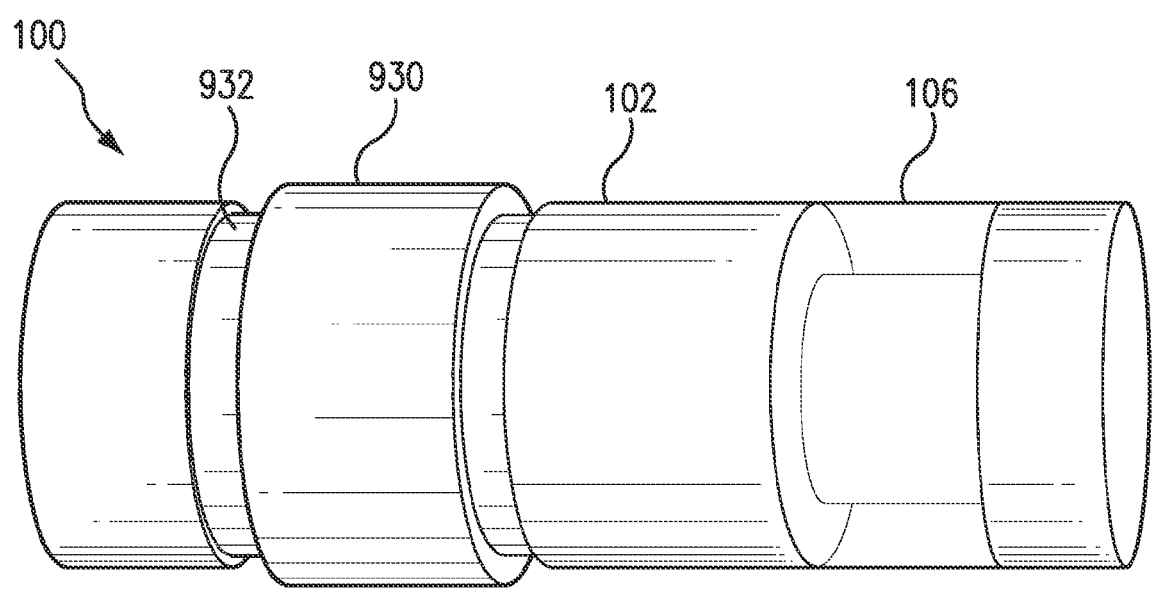

In some non-limiting embodiments, as illustrated in FIG. 9D, the sensor housing 102 may include a groove 932, and the ring-shaped drug-eluting polymer matrix 930 may be positioned in the groove 932. The edges of the groove 932 may assist in holding the ring-shaped drug-eluting polymer matrix 930 in place on the sensor housing 102.

In some non-limiting embodiments, the analyte indicator (e.g., polymer graft 106) may a have thin layer (e.g., 10 nm) on the outside of the graft 106. The thin layer may protect against indicator molecule degradation. The thin layer may be platinum, and the platinum may be sputtered onto the outside surface of the graft 106, which may include the indicator molecules 104. Platinum rapidly catalyzes the conversion of hydrogen peroxide into water and oxygen, which are harmless to the sensor. The rate of this reaction is much faster than the boronate oxidation; thus, the platinum would provide protection against oxidation by reactive oxygen species. Although platinum is the catalyst of the conversion of hydrogen peroxide into water and oxygen in some embodiments, in alternative embodiments, other catalysts of this reaction, such as, for example, palladium or catalase, may be used for the thin layer instead of or in addition to platinum.

Figure 9E:
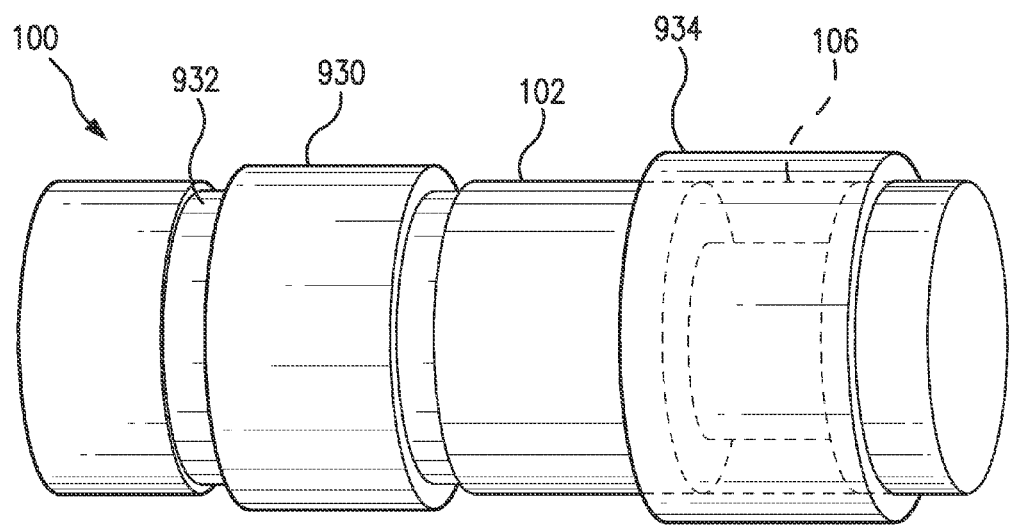

In some non-limiting embodiments, as illustrated in FIG. 9E, the sensor 100 may include a membrane 934 covering at least a portion of the analyte indicator. In one non-limiting embodiment, the membrane 934 may be an analyte permeable membrane. The membrane 934 may be positioned over the polymer graft 106 (and over any thin layer on the outside of the graft 106). The membrane 934 may be opaque and, therefore, perform a light-blocking function. In other words, the opaque nature of the membrane 934 may serve the function of effectively blocking the extraneous light from over stimulating the indicator molecules 104 of the graft 106. In some non-limiting embodiments, the opaque membrane 934 may be physically attached over the graft 106 after boring an additional, smaller well into the capsule/housing 102.

In some embodiments, the membrane 934 may be porous. In other words, the membrane 934 may be structured so that it channels one or more analytes (e.g., glucose) to the graft 106. For example, in one non-limiting embodiment, the membrane 934 may have small pores (e.g., pores having a pore size of microns or less) that block white blood cells (e.g., neutrophils), which are between 6 and 12 microns in diameter, from reaching the underlying graft 106 to attack it. The small pores, however, would at the same time be large enough to allow the analyte to reach the graft 106. In this way, a porous membrane 934 having small pores would increase sensor longevity while not affecting the ability of the sensor 100 to measure the analyte.

In some embodiments, the opaque membrane 934 may be made from a material that does not react adversely to the body's defenses. In non-limiting embodiments, the material from which the opaque membrane 934 is made may additionally be both porous (e.g., to allow and analyte, such as glucose, to flow through it) and opaque (e.g., to prevent light from traveling through it). For example, in some embodiments, the membrane (e.g., mesh) material may be a material such as nylon, cellulose acetate, polypropylene (PP), polyvinyl alcohol (PVA), polybutylene terephthalate (PBT), polyether ether ketone (PEEK), polyanhydride, polyamide, polyvinylchloride (PVC), polyethersulfone (PES), polyethylene terephthalate (PET), polyvinylidene difluoride (PVDF), polytetrafluoroethylene (PTFE), and/or polycarbonate.

In some embodiments, the membrane 934 may be a porous, opaque diffusion membrane that is configured to: substantially prevent white blood cells from passing through the membrane, permit an analyte of interest to pass through the membrane to the graft, and substantially prevent transmission of light of at least a specified wavelength or range of wavelengths through the membrane.

In some embodiments, to enhance biocompatibility and/or hydrophilicity, the membrane 934 may comprise an additional thin layer, and/or the membrane 934 may comprise multiple mesh layers. In some embodiments, the membrane 934 and the one or more therapeutic agents may have an additive effect in reducing oxidation of the analyte indicator.

In some embodiments, the sensor 100 may have one or more of the features described in U.S. patent application Ser. Nos. 14/142,000 and 14/142,017, filed on Dec. 27, 2013, which are incorporated herein by reference in their entireties.

In some embodiments, the one or more therapeutic agents, which may be dispersed within the drug eluting polymer matrix, may include one or more anti-inflammatory drugs, such as, for example, non-steroidal anti-inflammatory drug (e.g., acetylsalicylic acid (aspirin) and/or isobutylphenylpropanoic acid (ibuprofen)). In some non-limiting embodiments, the one or more therapeutic agents dispersed within the drug-eluting polymer matrix may include one or more glucocorticoids. In some non-limiting embodiments, the one or more therapeutic agents may include one or more of dexamethasone, triamcinolone, betamethasone, methylprednisolone, beclometasone, fludrocortisone, derivatives thereof, and analogs thereof. In some embodiments, the one or more therapeutic agents may reduce the production of hydrogen peroxide by neutrophils and macrophages. In some embodiments, the one or more therapeutic agents may reduce deterioration of the analyte indicator (e.g., polymer graft 106).

In some non-limiting embodiments, the drug eluting polymer matrix may release the one or more therapeutic agents distributed throughout the polymer matrix in a controlled manner. For instance, in various embodiments, the drug eluting polymer matrix may release the one or more therapeutic agents in a controlled manner over a period of hours, days, weeks, or months. FIG. 10 illustrates the release profile of dexamethasone acetate from a drug-eluting polymer matrix according to one non-limiting embodiment.

Figure 9F:
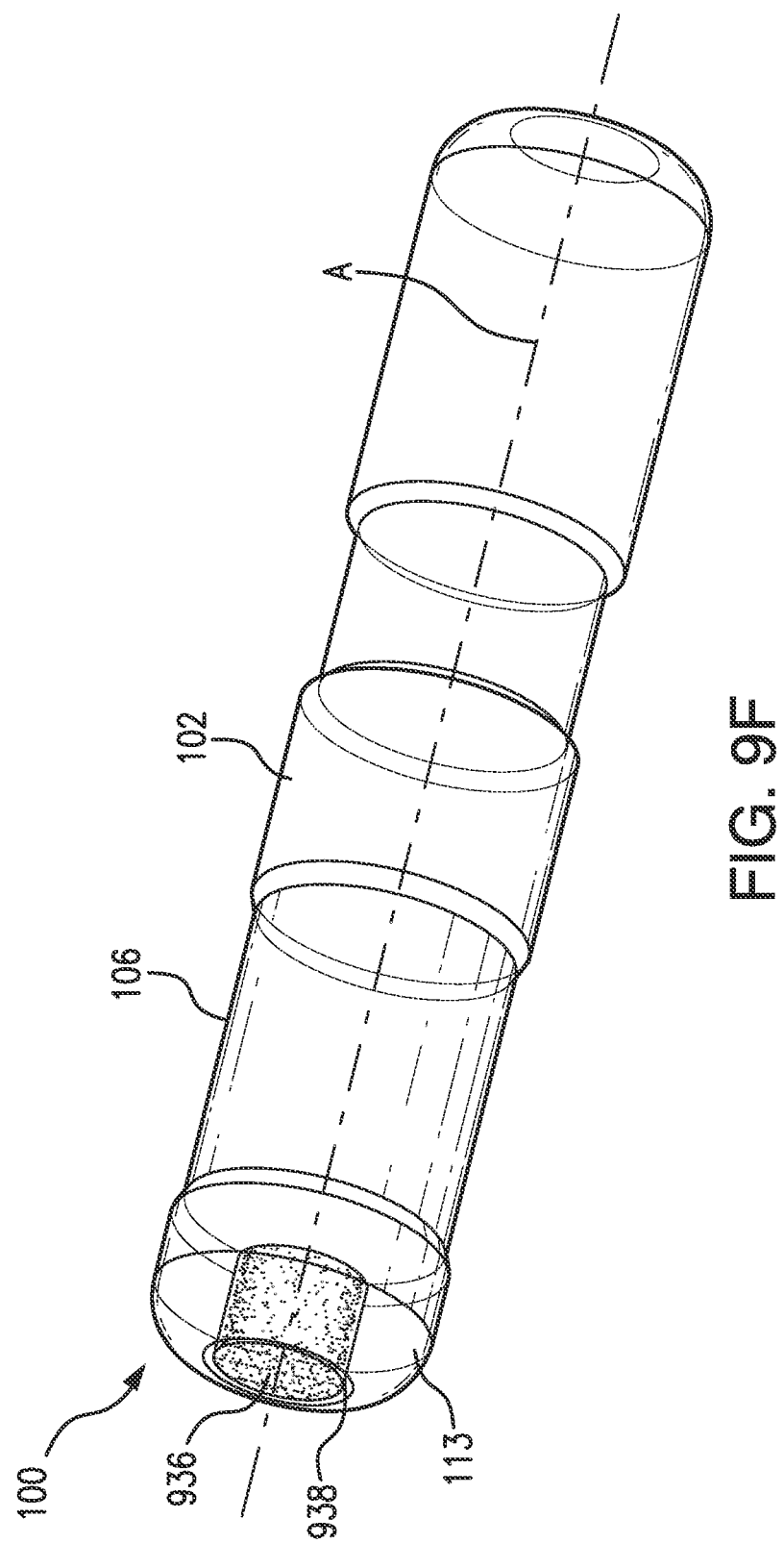
Figure 9G:
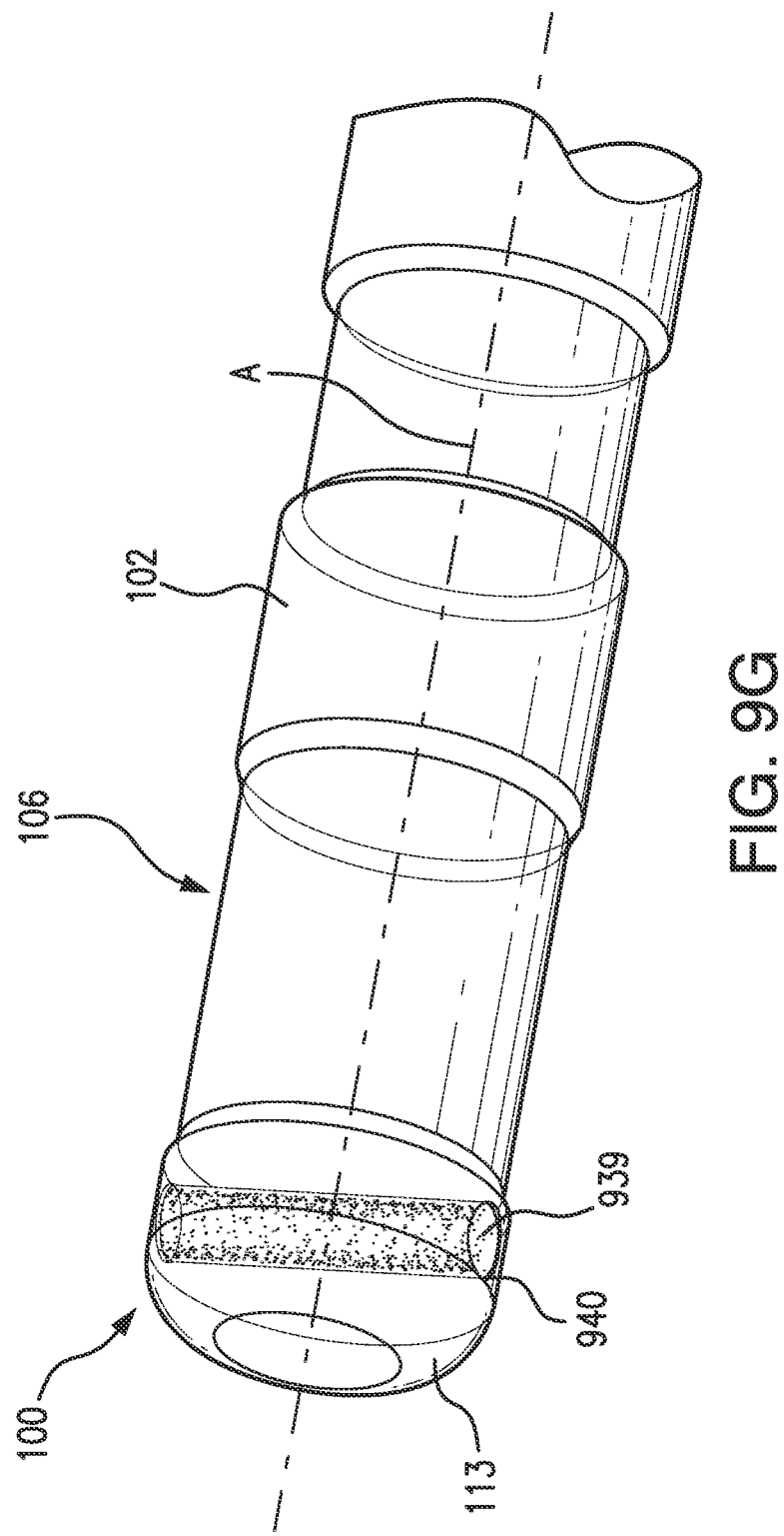

As described above, in some embodiments, the sensor 100 may include one or more drug eluting polymer matrices (e.g., drug-eluting polymer matrix 930) located outside the sensor housing 102 and covering at least a portion of the sensor housing 102. However, this is not required, and, in some embodiments, the sensor 100 may additionally or alternatively include one or more drug eluting polymer matrices located within the sensor housing. For example, as shown in FIGS. 9F and 9G, the sensor 100 may include a drug eluting polymer matrix 936 and 939, respectively, within the sensor housing 102. In some non-limiting embodiments, the sensor housing 102 may include one or more perforations (e.g., holes, openings, cavities, grooves, or channels), which may allow elution of the one or more therapeutic agents. For example, in the non-limiting embodiment illustrated in FIG. 9F, the drug eluting polymer matrix 936 may be in a form of a solid (e.g. cylinder) positioned in a hole or cavity 938 formed in an end portion of sensor housing 102 (e.g. end portion 113). In the embodiment of FIG. 9G, the hole or cavity 938 is formed in the direction substantially parallel to the longitudinal axis A of sensor 100. In other non-limiting embodiments, as illustrated in FIG. 9G, a drug eluting polymer matrix 939 may be in a form of a solid (e.g. cylinder) positioned in a channel or cavity 940 formed in an end portion sensor housing 102 (e.g. end portion 113). In the embodiment of FIG. 9G, the channel or cavity 940 is formed in the direction substantially orthogonal to the longitudinal axis A of sensor 100. Although the embodiment of FIG. 9G shows the drug eluting polymer matrix 940 extending from one end of the sensor to the opposite end, this is not necessary. In other embodiments, the channel or cavity 940 and/or the a drug eluting polymer matrix 939 may extend only a portion of the way into either one or both of either end of end portions of sensor housing 102. In some embodiments, by having the drug eluting polymer matrix 936 and/or 939 within the sensor housing 102, the sensor housing 102 may protect the drug eluting polymer matrix 936 and/or 939.

As described above, in some embodiments, the sensor 100 may include one or more therapeutic agents dispersed within one or more drug eluting polymer matrices (e.g., drug-eluting polymer matrix 930). However, this is not required, and, in some embodiments, one or more therapeutic agents may alternatively or additionally be incorporated within an analyte indicator (e.g., polymer graft 106) and/or a membrane (e.g., membrane 934) covering at least a portion of the analyte indicator. For example, in one non-limiting embodiment, the sensor 100 may not have a drug eluting polymer matrix and may instead have one or more therapeutic agents incorporated within a membrane that covers at least a portion of the analyte indicator. In another non-limiting embodiment, the sensor 100 may not have a drug eluting polymer matrix and may instead have one or more therapeutic agents incorporated within an analyte indicator (e.g., polymer graft 106), which may or may not be covered by a membrane. In yet another non-limiting embodiment, the sensor 100 may include a drug eluting polymer matrix (e.g., drug-eluting polymer matrix 930) and may also include one or more therapeutic agents incorporated within one or more of an analyte indicator and a membrane, which may cover at least a portion of the analyte indicator.

In some embodiments, the one or more therapeutic agents may be chemically incorporated within the drug eluting polymer matrix, membrane, or hydrogel and/or polymer containing the analyte indicator. In some non-limiting embodiments, one or more therapeutic agents may be incorporated within the drug eluting polymer matrix, membrane, or hydrogel and/or polymer containing the analyte indicator via covalent bonds. The drug eluting polymer matrix, membrane, or hydrogel and/or polymer containing the analyte indicator may release the one or more therapeutic agents when one or more of the covalent bonds are broken. For example, in one non-limiting embodiment, the covalent bonds may break in the presence of water (e.g., in the presence of water in the interstitial fluid, blood, or intraperitoneal fluid). However, this is not required, and, in some alternative embodiments, the covalent bonds may additionally or alternatively break through exposure to ultraviolet or visible light. In some non-limiting embodiments, the covalent bonds may break through exposure to light emitted by the light source 108. For example, in one embodiment, exposure to the excitation light 329 (e.g., having a wavelength of approximately 378 nm) emitted by the light source 108 may cause the covalent bonds to break. Moreover, the light source 108 may be controlled to emit light in a manner (e.g., blinking at specific intervals and/or intensities) that alters (e.g., increases the rate at which one or more therapeutic agents are released) the elution profile of the one or more therapeutic agents (e.g., to maximize effectiveness in preventing oxidation of the indicator species). In some embodiments, a wavelength in a specific range (e.g., 150 nm-1000 nm or 300-600 nm) may be necessary to photocleave (i.e., break the covalent bonds and release), and the wavelength of the light emitted by the light source 108 of the sensor 100 may be within in the specific range.

In some embodiments, the sensor 100 may include multiple drug eluting components. In some non-limiting embodiments, the sensor 100 may include any combination of one or more external drug eluting polymer matrices (i.e., drug-eluting polymer matrices located outside the sensor housing 102 and covering at least a portion of the sensor housing 102), one or more internal drug eluting polymer matrices (i.e., drug-eluting polymer matrices located within the sensor housing 102), one or more analyte indicators having one or more therapeutic agents incorporated therein, and/or one or more membranes covering at least a portion of an analyte indicator and having one or more therapeutic agents incorporated therein. For example, in one non-limiting embodiment, the sensor 100 may have two external drug eluting polymer matrices. In another non-limiting embodiment, the sensor 100 may have one external drug eluting polymer matrix, one internal drug eluting polymer matrix, and a membrane covering at least a portion of an analyte indicator and having one or more therapeutic agents incorporated therein.

In some embodiments, the multiple drug eluting components may have different elution/release rates. For example, in one non-limiting embodiment, the sensor 100 may include a first drug eluting polymer matrix and a second drug eluting polymer matrix, the first drug eluting polymer matrix may release one or more therapeutic agents dispersed within the first drug eluting polymer matrix at a first rate, and the second drug eluting polymer matrix may release one or more therapeutic agents dispersed within the second drug eluting polymer matrix at a second rate that is different from the first rate. For example, in one non-limiting embodiment, a faster release rate may be used on the initial immune response (e.g. 0-21 days), and a slower release rate may be used as a maintenance release to moderate any chronic immune response (e.g. 14-365+ days). In some embodiments, additional drug eluting components may have various rates of releasing one or more therapeutic agents.

Figure 11:
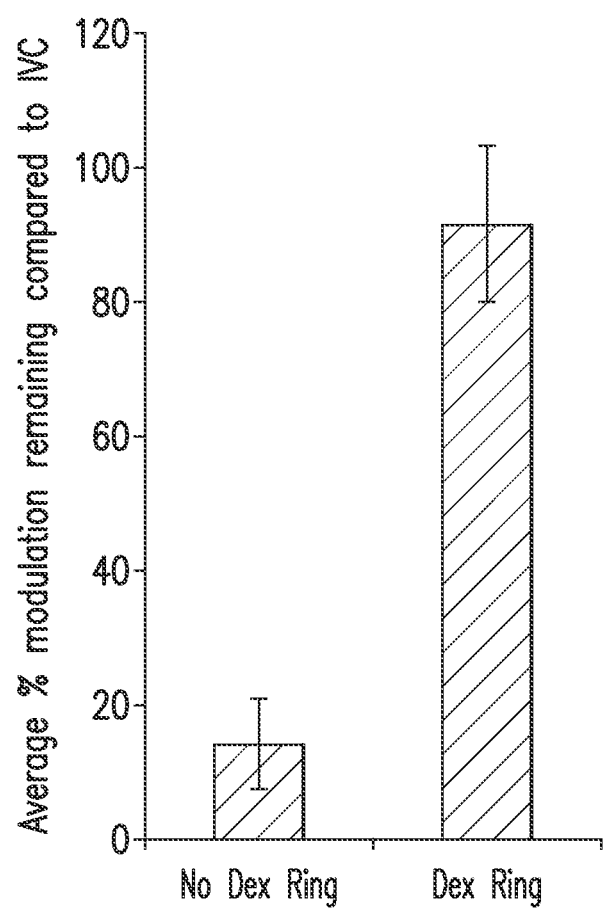
FIG. 11 is a graph showing experimental results comparing analyte modulation in sensors having no drug eluting polymer matrix with an embodiment of a sensor having a ring-shaped drug-eluting polymer matrix after 30 days in an animal model.

An implanted sensor including a drug-eluting polymer matrix, membrane, or analyte indicator may have improved performance over a sensor that does not include a drug-eluting polymer matrix. For instance, the controlled release of one or more therapeutic agents (e.g., by a drug-eluting polymer matrix) may have improved longevity and functionality. FIG. 11 is a graph showing the experimental results comparing analyte modulation in sensors having no drug eluting polymer matrix and no membrane 934 with a non-limiting embodiment of sensor 100 having a ring-shaped drug-eluting polymer matrix 930 after 30 days in an animal model (rat). FIG. 11 shows that, after 30 days in the animal model, the analyte indicators of the sensors having no drug eluting polymer matrix and no membrane 934 had an average modulation of approximately 15% relative to the modulation in in vitro conditions (IVC), where there is no immunological response. See results labeled "Sensor". In contrast, in the sensor having a drug-eluting polymer matrix, the analyte indicator had a modulation of greater than 90% relative to the modulation in IVC after 30 days in the animal model. See results labeled "Sensor+Dex". Thus, the non-limiting experimental results of the analyte indicator modulation of 30 days in the animal model show that a drug-eluting polymer matrix significantly increases sensor longevity and functionality.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, although in some embodiments, the analyte sensor 100 may be an optical sensor, this is not required, and, in one or more alternative embodiments, the analyte sensor may be a different type of analyte sensor, such as, for example, an electrochemical sensor, a diffusion sensor, or a pressure sensor. Also, although in some embodiments, the analyte sensor 100 may be an implantable sensor, this is not required, and, in some alternative embodiments, the analyte sensor may be a transcutaneous sensor having a wired connection to an external transceiver. For example, in some alternative embodiments, the analyte sensor 100 may be located in or on a transcutaneous needle (e.g., at the tip thereof). In these embodiments, instead of wirelessly communication using an antenna (e.g., inductive element 114), the analyte sensor may communicate with the external transceiver using one or more wires connected between the external transceiver and a transceiver transcutaneous needle including the analyte sensor. For another example, in some alternative embodiments, the analyte sensor may be located in a catheter (e.g., for intravenous blood glucose monitoring) and may communicate (wirelessly or using wires) with an external transceiver.

What is claimed is:

1. A sensor for measurement of an analyte in a medium within a living animal, the sensor comprising:
    a sensor housing;
    a light source within the sensor housing configured to emit excitation light;
    an analyte indicator covering a portion of the sensor housing, wherein the analyte indicator comprises one or more indicator molecules that reversibly bind the analyte, are positioned to be irradiated by the excitation light, and are configured to emit light indicative of the amount of the analyte in the medium within the living animal;
    a photodetector within the sensor housing, wherein the photodetector is sensitive to light emitted by the one or more indicator molecules and configured to generate a signal indicative of the amount of the analyte in the medium within the living animal;
    at least one drug eluting polymer matrix that covers a portion of the sensor housing and is separate and distinct from the analyte indicator, wherein the drug eluting polymer matrix (a) has a preformed shape and is applied to the sensor housing attaching the preformed shape to the sensor housing or (b) is applied to the sensor housing via dip coating or spray coating; and
    one or more therapeutic agents that reduce deterioration of the analyte indicator, are dispersed within the drug eluting polymer matrix, and include an anti-inflammatory drug.

2. The sensor of claim 1, wherein the sensor is implantable within a living animal.

3. The sensor of claim 1, wherein the drug eluting polymer matrix is applied to the sensor housing via dip coating or spray coating.

4. The sensor of claim 1, wherein one or more of the therapeutic agents are incorporated within the drug eluting polymer matrix via one or more covalent bonds that break in the presence of aqueous media and release the one or more therapeutic agents.

5. The sensor of claim 1, wherein one or more of the therapeutic agents are incorporated within the drug eluting polymer matrix via one or more covalent bonds that break through exposure to light and release the one or more therapeutic agents.

6. The sensor of claim 5, wherein the covalent bonds break through exposure to light emitted by the light source.

7. The sensor of claim 1, wherein the drug eluting polymer matrix has a preformed shape.

8. The sensor of claim 7, wherein the preformed shape is a ring.

9. The sensor of claim 7, wherein the preformed shape is a sleeve.

10. The sensor of claim 7, wherein the preformed shape is a conformal shell.

11. The sensor of claim 7, wherein the preformed shape is a cylinder.

12. The sensor of claim 7, wherein the preformed shape is a monolith.

13. The sensor of claim 12, wherein the monolith is a rectangular monolith.

14. The sensor of claim 1, wherein the drug eluting polymer matrix is adjacent to the analyte indicator.

15. The sensor of claim 1, wherein the analyte indicator has a first side and a second side, and wherein the drug eluting polymer matrix is located adjacent to the analyte indicator on the first side and the second side of the analyte indicator.

16. The sensor of claim 1, wherein the analyte indicator is located in a polymer matrix.

17. The sensor of claim 16, wherein one or more therapeutic agents are incorporated in the analyte indicator polymer matrix.

18. The sensor of claim 1, wherein the anti-inflammatory drug is a non-steroidal anti-inflammatory drug.

19. The sensor of claim 18, wherein the non-steroidal anti-inflammatory drug is acetylsalicylic acid.

20. The sensor of claim 18, wherein the non-steroidal anti-inflammatory drug is isobutylphenylpropanoic acid.

21. The sensor of claim 1, wherein the one or more therapeutic agents include a glucocorticoid.

22. The sensor of claim 1, wherein the one or more therapeutic agents include one or more of dexamethasone, triamcinolone, betamethasone, methylprednisolone, beclometasone, fludrocortisone, derivatives thereof, and analogs thereof.

23. The sensor of claim 1, wherein the one or more therapeutic agents reduce oxidation of the analyte indicator.

24. The sensor of claim 1, wherein the analyte indicator is a graft.

25. The sensor of claim 1, further comprising a layer of a catalyst on at least a portion of the analyte indicator, wherein the catalyst is capable of converting hydrogen peroxide into water and oxygen.

26. The sensor of claim 1, further comprising a membrane covering at least a portion of the analyte indicator.

27. The sensor of claim 26, wherein the membrane is a porous, opaque diffusion membrane.

28. The sensor of claim 26, wherein the membrane is configured to:
    prevent white blood cells from passing through the membrane, permit an analyte of interest to pass through the membrane to the graft, and prevent transmission of light of at least a specified wavelength or range of wavelengths through the membrane.

29. The sensor of claim 26, wherein one or more therapeutic agents are incorporated within the membrane.

30. The sensor of claim 29, wherein one or more of the therapeutic agents incorporated within the membrane are incorporated within the membrane via one or more covalent bonds that break in the presence of an aqueous media and release the one or more therapeutic agents.

31. The sensor of claim 29, wherein one or more of the therapeutic agents are incorporated within the membrane via one or more covalent bonds that break through exposure to light and release the one or more therapeutic agents.

32. The sensor of claim 31, wherein the covalent bonds break through exposure to light emitted by the light source.

33. The sensor of claim 32, where in light is UV or visible light.

34. The sensor of claim 1, further comprising a first drug eluting polymer matrix and a second drug eluting polymer matrix, wherein the one or more therapeutic agents are dispersed within the first drug eluting polymer matrix, and one or more therapeutic agents are dispersed within the second drug eluting polymer matrix.

35. The sensor of claim 34, wherein the first drug eluting polymer matrix releases the one or more therapeutic agents dispersed within the first drug eluting polymer matrix at a first rate, and the second drug eluting polymer matrix releases the one or more therapeutic agents dispersed within the second drug eluting polymer matrix at a second rate that is different from the first rate.

36. A sensor for measurement of an analyte in a medium within a living animal, the sensor comprising:
   a sensor housing;
   an analyte indicator covering a portion of the sensor housing;
   a layer of a catalyst on at least a portion of the analyte indicator, wherein the layer of catalyst facilitates the conversion of hydrogen peroxide into water and oxygen;
   at least one drug eluting polymer matrix that covers a portion of the sensor housing and is separate and distinct from the analyte indicator, wherein the drug eluting polymer matrix (a) has a preformed shape and is applied to the sensor housing attaching the preformed shape to the sensor housing or (b) is applied to the sensor housing via dip coating or spray coating; and
   one or more therapeutic agents dispersed within the at least one drug eluting polymer matrix, wherein the one or more therapeutic agents reduce deterioration of the analyte indicator and include an anti-inflammatory drug.

37. The sensor of claim 36, wherein one or more therapeutic agents that reduce deterioration of the analyte indicator are incorporated within the analyte indicator.

38. The sensor of claim 36, further comprising a membrane covering at least a portion of the analyte indicator.

39. The sensor of claim 38, wherein one or more therapeutic agents that reduce deterioration of the analyte indicator are incorporated within the membrane.

40. The sensor of claim 36, further comprising a light source within the sensor housing and a photodetector within the sensor housing;
   wherein the light source is configured to emit excitation light;
   wherein the analyte indicator comprises one or more indicator molecules that reversibly bind the analyte, are positioned to be irradiated by the excitation light, and are configured to emit light indicative of the amount of the analyte in the medium within the living animal;
   wherein the photodetector is sensitive to sensitive to light emitted by the one or more indicator molecules and configured to generate a signal indicative of the amount of the analyte in the medium within the living animal.

* * * * *